US006455051B1

(12) United States Patent
Hayashi et al.

(10) Patent No.: US 6,455,051 B1
(45) Date of Patent: Sep. 24, 2002

(54) AMELIORANT FOR HEPATITIS C THERAPEUTIC EFFECT AND APPLICATION THEREOF

(75) Inventors: Norio Hayashi, Kawanishi; Yuji Kito, Nagaokakyo; Aya Furukawa, Osaka, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/529,303

(22) PCT Filed: Oct. 13, 1998

(86) PCT No.: PCT/JP98/04621

§ 371 (c)(1),
(2), (4) Date: Apr. 12, 2000

(87) PCT Pub. No.: WO99/18993

PCT Pub. Date: Apr. 22, 1999

(30) Foreign Application Priority Data

Oct. 13, 1997 (JP) ............................................. 9-278505

(51) Int. Cl.[7] .................... A61K 39/29; A61K 38/21; A61K 45/00
(52) U.S. Cl. .................. 424/228.1; 424/85.4; 424/85.5; 514/894
(58) Field of Search ............................. 424/85.4, 85.5, 424/228.1; 514/894

(56) References Cited

U.S. PATENT DOCUMENTS 5,082,659 A   1/1992   Fleischmann

FOREIGN PATENT DOCUMENTS

| EP | 107 498   | 5/1984  |
| EP | 294160    | 12/1988 |
| EP | 790062    | 8/1997  |
| JP | 7-258109  | 10/1995 |
| JP | 9-216831  | 8/1997  |

OTHER PUBLICATIONS

Weigent, D.A. et al., "Potentiation of Lymphocyte Natural Killing by Mixtures of Alpha or Beta Interferon with Recombinant Gamma Interferon, Infection and Immunity", 1983, vol. 40, No. 1, pp. 35–38. (Copy submitted to USPTO by WIPO).

Hoofnagle, J.H. et al., "Treatment of Non–A, Non–B Hepatitis with Recombinant Human Alpha Interferon", New Engl. J. Med., 1986, vol. 315, No. 25, pp. 1575–1578, cited in the present application. (Copy submitted to USPTO by WIPO).

"Synergistic Antiviral and Antiproliferatve Activities of Escherichia coli–Derived Human Alpha, Beta, and Gamma Interferons" by Czarniecki et al., Journal of virology, Feb. 1984, pp. 490–496.

"Potentiation of the Antiviral and Anticellular Activities of Interferons by Mixtures of HuIFN— and HIFN— or HuIFN—" by Oleszak et al., Journal of Interferon Research 5: 361–371 (1985).

"Potentiation of Interferon— In Vitro Antiviral Activity by Interferon– Is Not Abrogated by Antibody to Interferon–" by Capobianchi et al., Journal of Interferon Research 13: 53–55 (1993).

"A Pilot Study of Natural Interferon Therapy for Chronic Hepatitis C" by Sata et al., Intl. Hepatology Communications 6 (1997) pp. 264–373.

"Mechanism of Interferon Action: Human Leukocyte and Immune Interferons Regulate the Expression of Different Genes and induce Different Antiviral States in Human Amnion U Cells" by Samuel et al., Virology 130, 474–484 (1983).

"Therapy of Chronic Hepatitis B with Recombinant Human Alpha and Gamma Interferon" by Bisceglie et al., Hepatology vol. 11, No. 2 (1990) 266–270.

"High Doses of Recombinant –Interferon or –Interferon for Chronic Hepatitis C: A Randomized, Controlled Trial" by Saez–Royuela et al., Hepatology vol. 13, No. 2 (1991) pp. 327–331.

"Interferon Therapy for non–A, non–B Chronic Hepatitis" by Iino et al., Gastroenterologia Japonica, vol. 26, Suppl. 3, 1991, pp. 224–229.

"Treatment of Chronic Hepatitis C with Recombinant Interferon Alfa—A Multicenter Randomized, Controlled Trial" by Davis et al., The New England Journal of Medicine, vol. 321, No. 22, 1989, pp. 1501–1506.

"High Doses of Recombinant α–Interferon or γ–Interferon for Chronic Hepatitis C: A Randomized, Controlled Trial" by Sáez–Royuela et al., Hepatology, vol. 13, No. 2, 1991 pp. 327–331.

"Retreatment with 24–Week Course of Interferon –α for Patients with Chronic Hepatitis C" by Hagiwara et al., International Hepatology Communications 5, 1996, pp. 135–142.

(List continued on next page.)

Primary Examiner—Jeffrey Stucker
Assistant Examiner—Jegatheesan Seharaseyon
(74) Attorney, Agent, or Firm—Sughrue Mion, PLLC

(57) ABSTRACT

The present invention provides an ameliorant for enhancing the therapeutic effect of IFN-α on hepatitis C; a therapeutic composition for the treatment of hepatitis C which comprises IFN-α and IFN-γ as active ingredients and further contains a pharmaceutically acceptable carrier; a kit for the treatment of hepatitis C which comprises an IFN-α preparation and an IFN-γ preparation; and a therapeutic method for the treatment of hepatitis C which comprises administering IFN-α and IFN-γ to a subject at the same time or administering IFN-γ before the administration of IFN-α. The present invention is capable of making the patient continuously HCV-RNA negative and is extremely useful in the treatment of chronic hepatitis C which is intractable with, IFN-α and conventionally difficult to remedy.

13 Claims, No Drawings

OTHER PUBLICATIONS

"A Pilot Study of Natural Interferon γ Therapy for Chronic Hepatis C", Sata et al., International Hepatology Communications 6, 1997, pp. 264–273.

"Therapy of Interferon Resistant Chronic Hepatitis Type C," Advances in Medicine, vol. 161, No. 5, May 2, 1992, pp. 389–392.

"Chronic Hepatitis C: Measures to Be Taken in Non–Interferon–Responding Cases," Internal Medicine, vol. 72, No. 5, Nov. 1993, pp. 873–882.

"Therapy of Chronic Hepatitis C–Interferon Therapy in Particular–What should Be Done in Non–IFN–Responding Cases," Therapy, vol. 75, No. 4, Apr. 1993, pp. 111–118.

"Therapeutic Results and Problems In Chronic Hepatitis C Interferon Retreatment Cases," Medical Practice, vol. 10, No. 5, 1993, pp. 981–983.

"Interferon (IFN) Side Effects and Remedies," Kantansui 21(5), 1990, pp. 899–904.

AMELIORANT FOR HEPATITIS C THERAPEUTIC EFFECT AND APPLICATION THEREOF

TECHNICAL FIELD

The present invention relates to an ameliorant for hepatitis C therapeutic effects, the ameliorant being used in combination with interferon-α (hereinafter referred to as "IFN-α"). More specifically, the present invention relates to an ameliorant for hepatitis C therapeutic effects, which is used together with IFN-α or before the administration of IFN-α and has the action of improving or enhancing the therapeutic effects of IFN-α on hepatitis C.

The present invention further relates to a therapeutic composition for the treatment of hepatitis C, which has high therapeutic effects on hepatitis C, as compared to conventional hepatitis C therapeutic agents comprising IFN-α as an active ingredient.

The present invention further relates to a pharmaceutical kit for the treatment of hepatitis C, which comprises a pharmaceutical composition containing IFN-α as an active ingredient and a pharmaceutical composition containing interferon-γ (hereinafter referred to as "IFN-γ") as an active ingredient.

The present invention further relates to an effective therapeutic method for the treatment of hepatitis C.

BACKGROUND ART

In chronic hepatitis C, as long as hepatitis C virus (HCV) infection continues, liver lesion does not cure and the alleviation is rare. About 40% of chronic hepatitis C patients progress to liver cirrhosis, and further 25% develop hepatocellular carcinoma. Of the liver cirrhosis cases, 75% progress from chronic hepatitis. It is therefore recognized that chronic hepatitis should be actively treated without viewing the prognosis optimistically.

Since infection of hepatitis C virus (HCV) which is a RNA virus causes hepatitis C, IFN-α or interferon-β (herein after referred to as "IFN-β") presumably having the action of suppressing the proliferation of HCV may cure chronic hepatitis C. From such theoretical background, an IFN-α therapy for the treatment of non-A non-B chronic hepatitis was reported in 1986 by Hoofnagle et al. (Hoofnagle, J. H., Mullen, K. D., et al.: N. Engl. J. Med., 315, 1575–1578, 1986), and attracted attention. HCV was identified in 1988, and it has been proven that 90% of the non-A non-B chronic hepatitis cases are chronic hepatitis C.

In Japan, various IFN-α or IFN-β therapeutic methods have been tested since about 1988, and their clinical use was permitted in 1992.

At present, as IFN-α therapy for the treatment of chronic hepatitis C, a method of administering IFN-α three times weekly for a long period of time (Davis, G. L., Balart, L. A.,: N. Engl. J. Med., 321, 1501–1506, 1989) is used in the U.S., Europe and part of Japan, whereas a method of administering a large amount of IFN-α every day for the first 2 to 4 weeks of IFN-α administration (Iino, S., Hino, K., et al.: Gastroent. Jpn., 26(Suppl.3), 224–239, 1991) is employed in Japan.

In the former method, the daily dose of IFN-α is 3~5×10$^6$ IU in many cases. In such cases, GPT (glutamic-pyruvic transaminase) decreases well during the administration of IFN-α, but GPT increases again and HCV-RNA reappears in most cases when the administration of IFN-α is stopped. In recent research, a report shows that administration of IFN-α (3×10$^6$ IU) three times,weekly for 18 to 24 months makes 24% of the patients continuously HCV-RNA negative, thus enhancing therapeutic effects on chronic hepatitis C, as compared to the 6-month administration whereby the HCV-RNA continuous negative rate is 12.5% (F.D.C Reports, Mar. 31, 1997). Based on the report, the FDA has approved the 12-month administration as a preferable IFN-α administration method.

In the latter method, i.e., method of administering a large amount of IFN-α every day for the first 2 to 4 weeks of IFN-α administration, a daily IFN-α dose of as high as 10×10$^6$ IU is expected to achieve a continuous normalization of GPT in 40 to 50% of the patients even after the completion of administration and make 30 to 40% of the patients HCV-RNA negative. With such expectation, this method is used in Japan.

In Japan, a method of administering IFN-β every day for 6 to 8 weeks is also widely used as a therapy for chronic hepatitis C.

As regards IFN-γ, it has been reported that IFN-γ produced no effects when administered to 10 chronic hepatitis C patients for 6 months (F. Saez-Royuela, et al.: Hepatology, 13: 327–331, 1991). Michio Sata et al (International Hepatology Communications 6 (1997) 264–273) reported on the expression of the immunological action of IFN-γ, but the effectiveness has not been officially recognized yet.

As shown above, IFN-α therapy and IFN-β therapy are conventionally used for the treatment of chronic hepatitis C. In recent year, factors determining the therapeutic effects of IFN-α and IFN-β have been elucidated.

The background factors affecting IFN-α therapy were analyzed dividing the patients into an IFN-α therapy responsive group whose IFN-α intermittent administration period was less than 2 years and into an IFN-α therapy resistant group whose IFN-α intermittent administration period was 2 years or more. The analysis revealed that HCV genotype, HCV quantity before the treatment and liver image are important. More specifically, the analysis revealed that IFN-α therapy and IFN-β therapy are effective against chronic hepatitis cases wherein the HCV genotype is 2a or 2b, the HCV amount is less than 10$^6$ copies/ml (1 Meq/ml) and the fibrillation is slight, whereas it is less effective against chronic hepatitis cases wherein the HCV genotype is 1a or 1b, the HCV amount is 10$^6$ copies/ml (1 Meq/ml) or more and the fibrillation is moderate to severe. Age, sex, contraction period, biochemical test values did not greatly affect IFN-α or IFN-β therapeutic effects.

The antiviral action and side effects of IFN-α or IFN-β are dose-dependent, although there are some individual differences. In IFN-α or IFN-β therapies, it is therefore expected that an increased dose of IFN enhances antiviral effects and produces high therapeutic effects, whereas undesirable side effects of IFN-α or IFN-β are worried about. A long-term administration of IFN is better as mentioned above, but causes various side effects, for example, (1) having the possibility that the antibody neutralizes recombinant IFN, (2) inducing autoimmune diseases, (3) producing side effects on the cardiovascular system and (4) inducing or worsening the side effects on patients with depression (Shiro Itano; liver bile pancreas, 21,899–904, 1990).

Therefore, an effective therapeutic method for treating chronic hepatitis C patients who have not responded to IFN-α or IFN-β treatment is sought now.

There are few research reports on the retreatment cases of IFN-α-ineffective chronic hepatitis C patients using IFN-α. From the reports, however, there appear to be two types of IFN-α-ineffective chronic hepatitis C patients, i.e., the cases in which IFN was ineffective because of an insufficient dosage or short administration period in the first treatment and the cases in which IFN was ineffective despite a sufficient IFN administration.

Kuroki et al. (Tetsuo Koroki: Medical Practice, 10,981, 1993) administered IFN-α again to 18 out of 71 patients who had not responded to the first IFN-α administration and examined their condition for 1 year or more. Kuroki et al. reported that of the 18 patients, only 1 patient (6%) had continuous normalization of GPT (remarkable efficacy) and there was no continuous HCV-RNA negative case.

Matsushima (Takashi Matsushima: Treatment, 77, 1187, 1983) reports the results of re-administration of IFN-α to 37 patients who had been judged as unchanged cases in the first IFN-α administration. The results show that the GPT continuous normalization rate achieved by re-administering IFN-α to 27 patients who had shown transient effects in the first IFN-α administration was 22.2% (6/27 cases), whereas re-administration of IFN-α to 10 patients who had not responded to the first IFN-α administration at all produced no effects (0/10 cases). After all, the GPT continuous normalization rate achieved by re-administration of IFN-α to the unchanged cases was as low as 16.2% (6/37 cases).

Hagiwara et al (H. Hagiwara, et al.: Int. Hepatology Communications, 5, 135–142, 1996) reports that as a result of re-administering IFN-α (6 MU) three times weekly for 24 weeks to 29 patients having failed to respond to the first IFN-α administration, 3 patients (10%) had a continuous normalization of GPT and HCV-RNA continuous negative rate was 10% (3/29 cases).

According to Arakawa et al. (Yasuyuki Arakawa, Hitoshi Okubo: Internal Medicine, 72(5), 873–882, 1993), as a result of retreatment of 19 chronic hepatitis C patients with IFN-α, effective cases were four cases (21%). A comparison of the efficacy of IFN-α re-administration according to HCV-RNA types shows that as regards type 1b, the effective case was only one (6.7%) out of 15 cases, and the other 14 cases (93.3%) were ineffective cases. As for type 2a, the effective cases were 2 out of 3 cases (66.7%) and the ineffective case was one (33.3%). As for type 2b, the effective case was only one. Further, the third IFN-α administration to 3 out of the 14 patients with type 1b hepatitis incurable with the second administration was ineffective in any case.

As shown above, about 80% of the patients having failed to respond to the first IFN-α administration are resistant to the retreatment with IFN-α, and the retreatment is ineffective. Especially, re-administration of IFN-α produces little effects on hepatitis of type 1a or 1b which is considered to be intractable to IFN-α. From the above facts, it can be said that efficacy of IFN-α or IFN-β therapy against chronic hepatitic C of type 1a or 1b with a large amount of virus is extremely low and there is no method for treating IFN-ineffective cases at present. If chronic hepatitis C is regarded as an infectious disease of the liver by hepatitis C virus (HCV), the target of the treatment is the virus, and treatment for the HCV eradication using IFN-α should be more effective. However, contrary to expectation, a large expectation can not be currently placed on the IFN-α re-administration to IFN-α-ineffective patients, as is clear from the above results.

As mentioned above, it is said that the efficacy of IFN-α against chronic hepatitis C is about 30%. Although various IFN-α administration methods are being tried in order to increase the efficacy, a satisfactory therapeutic method has not been established yet. Especially, there is desired the development of an effective therapeutic method for the treatment of IFN-α intractable chronic hepatitis C, i.e., hepatitis of type 1a or 1b with a virus amount of as high as $10^6$ copies/ml (1 Meq/ml) or more.

The present invention has been developed in view of the above circumstances. An object of the present invention is to provide an ameliorant for hepatitis C therapeutic effects, which is used in combination with IFN-α so as to produce therapeutic effects even on IFN-α intractable chronic hepatitis C, thus producing high therapeutic effects.

In this specification, IFN-α intractable (chronic) hepatitis C means the case in which at least one of the following conditions are satisfied: (i) the HCV genotype is 1a or 1b, (ii) the HCV amount in the patient is as high as $10^6$ copies/ml (1 Meq/ml) or more, and (iii) the fibrillation is moderate to severe.

Another object of the invention is to provide a therapeutic composition for the treatment of hepatitis C comprising IFN-α and the above ameliorant, especially a therapeutic composition for the treatment of IFN-α intractable chronic hepatitis C.

The hepatitic C therapeutic composition and the ameliorant for hepatitis C therapeutic effects have the effects of alleviating the side effects of conventional IFN-α preparations.

A further object of the invention is to provide a kit for the treatment of hepatitis C comprising an IFN-α preparation and an IFN-γ preparation, the kit being useful for the treatment of hepatitis C, especially IFN-α intractable chronic hepatitis C.

A further object of the invention is to provide a therapeutic method for the treatment of hepatitis C, which has especially high therapeutic effects on IFN-α intractable chronic hepatitis C.

DISCLOSURE OF THE INVENTION

The present inventors carried out intensive research to achieve the above objects and found that when IFN-α is administered to IFN-α intractable chronic hepatitis C patients after administration of IFN-γ, chronic hepatitis C is alleviated very well. The present inventors further found that similar effects are achieved by administering IFN-α in combination with IFN-γ.

As mentioned earlier, it is conventionally known that IFN-α and IFN-γ have antiviral action. As regards the viruses on which a single agent of IFN-α or IFN-γ has antiviral action, combined use of IFN-α and IFN-γ is expected to produce higher antiviral action than a single use of IFN-α or IFN-γ in theory. In reality, however, viruses on which combined use of IFN-α and IFN-γ produces no synergistic or additive effect are reported (C. E. Samuel et al., Virology, 130, 474–484, 1983; AM Di Bisceglie et al, Hepatology, 11(2), 266–270, 1990).

As mentioned already, it has been confirmed by administering IFN-γ to chronic hepatitis C patients that IFN-γ has no antiviral effect on HCV (Yasuyuki Ota, Norio Horiuke, Progress of Medicine, 161(5),389–392, 1992; F. Saez-Royuela et al., Hepatology, 13, 327–331, 1991; Michio Sata et al., International Hepatology Communications 6 (1997) 264–273).

Therefore, it is actually unpredictable that combined use of IFN-α and IFN-γ can effectively alleviate hepatitis C. Especially the following finding in the present invention is surprising: even IFN-α intractable chronic hepatitis C can be significantly alleviated by combined use of IFN-α and IFN-γ, preferably by administration of IFN-γ prior to the IFN-α administration.

The present invention has been developed based on the above finding. The present invention includes the following interferon (IFN) preparations.

1. An ameliorant capable of enhancing the therapeutic effects of IFN-α on hepatitis C, the ameliorant comprising IFN-γ as an active ingredient.
2. A therapeutic composition for the treatment of hepatitis C, which comprises IFN-α and IFN-γ as active ingredients and further contains a pharmaceutically acceptable carrier.

The combined use of the ameliorant of the above item 1 with IFN-α or the use of the hepatitis C therapeutic composition of item 2 produces therapeutic effects on IFN-α intractable hepatitis C which has not been cured with a sufficient amount of IFN-α alone. Therefore, the above ameliorant and hepatitis C therapeutic composition are highly useful for the treatment of IFN-α intractable hepatitic C.

Further, the present invention provides 3. a kit for the treatment of hepatitis C comprising an IFN-α preparation and an IFN-γ preparation, the kit being useful for the treatment of hepatitis C, especially IFN-α intractable hepatitis C.

Further, the present invention provides the following therapeutic methods for the treatment of hepatitis C.

4. A therapeutic method for the treatment of hepatitis C, which comprises administering IFN-α and IFN-γ to a subject at the same time or administering IFN-γ before the administration of IFN-α.
5. A therapeutic method for the treatment of hepatitis C which comprises administering IFN-γ to a subject before the administration of IFN-α.

These therapeutic methods are especially useful for the treatment of IFN-α intractable hepatitis C.

Further, the present invention provides the following novel uses of IFN-γ.

6. Use of IFN-γ for producing an ameliorant capable of enhancing therapeutic effects of IFN-α on hepatitis C.
7. Use of interferon-γ for producing a therapeutic composition for the treatment of hepatitis C, the composition comprising IFN-α and IFN-γ as active ingredients.

The ameliorant for hepatitis C therapeutic effects of the invention is an adjuvant having the action of improving or enhancing the therapeutic effects of IFN-α on hepatitis C and producing therapeutic effects on IFN-α intractable hepatitis C, and comprises IFN-γ as an active ingredient.

IFN-γ used in the invention can be any of those clinically used and may be of natural type or recombinant type.

The ameliorant of the invention is not limited specifically in administration timing, administration route, administration form and dosage, as long as the desired effects are produced.

As regards the administration timing, 1) a method of administering the ameliorant before the administration of IFN-α, and 2) a method of administering the ameliorant simultaneously with the administration of IFN-α can be mentioned. In the method 2), the ameliorant of the invention may also be used by incorporation into the hepatitis C therapeutic composition comprising IFN-α as an active ingredient.

Preferable is a method of administering an IFN-γ-containing ameliorant of the invention before the administration of IFN-α, or a method of administering an IFN-γ-containing ameliorant of the invention simultaneously with the administration of IFN-α. The most preferable is a method of administering the ameliorant of the invention before the administration of IFN-α.

In the case of administering the IFN-γ-containing ameliorant of the invention before the administration of IFN-α, as long as the administration steps of "IFN-γ administration→IFN-α administration" are maintained, an IFN-γ pharmaceutical or an IFN-α pharmaceutical may be administered once or several times without limitation, before or after the administration steps. For example, the administration method may comprise IFN-α administration→IFN-γ administration→IFN-α administration, or comprise IFN-γ administration→IFN-α administration→IFN-γ administration.

The ameliorant of the invention is not specifically limited in administration route, either and can be administered by any of the IFN pharmaceutical administration methods used at present or approved in future. Examples are oral administration, parenteral administration, local administration, general (whole body) administration and the like. Preferable is parenteral administration. For example, local administration such as intramascular injection or general administration such as intravenous injection can be used. More preferable are intramuscular administration such as intramuscular injection and subcutaneous administration.

The ameliorant of the invention can be shaped into any form such as solids and semi-solids or liquids according to the administration method. Examples of solid pharmaceuticals are tablets, capsules, pills, powders (powdered medicine) or granules, suppositories, etc. Examples of liquid pharmaceuticals are liquids, suspensions or emulsions for oral administration and injections, drops (including suspensions, emulsions, etc.) and like parenteral medicine. These pharmaceuticals are prepared by conventional pharmaceutical methods known in the art.

The ameliorant of the invention essentially comprises IFN-γ and may further contain pharmaceutically acceptable carriers or various kinds of additives such as buffers, stabilizers, colorants, preservatives, aromatics, flavors or sweetening agents.

There is no specific limitation on the kinds and amounts of the pharmaceutically acceptable carriers, as long as they do not counteract hepatitis C treatment enhancing effects of IFN-γ on IFN-α. The kind and the amount may be suitably selected in accordance with the pharmaceutical form and conventional method in the art.

When the ameliorant of the invention is to be provided in an injectable form such as such as a solution, an emulsion or a suspension, the preparation is preferably sterilized and rendered isotonic to the blood. Diluents for use in such preparation include, for example, water, ethanol, macrogols, propylene glycol, ethoxylated isostearyl alcohol, polyoxyisostearyl alcohol, polyoxyethylene sorbitan fatty acid esters and the like. In this case, sodium chloride, glucose or glycerin may be added to the pharmaceutical composition of the invention in an amount sufficient to provide an isotonic solution. Conventional solubilizers, buffers, anesthetics etc. may also be added.

Similarly, there is no specific limitation on the kinds and amounts of the additives, as long as they do not counteract hepatitis C treatment enhancing effects of IFN-γ on IFN-α and do not produce any side effects. The kind and the amount may be suitably selected in accordance with the pharmaceutical form and conventional method in the art.

For example, the stabilizing agent may be any of the pharmaceutically acceptable ones and includes, for example, human serum albumins, saccharides, amino acid and like substances generally used as protein stabilizers. The human serum albumin may be of natural type or gene recombinant type. Examples of saccharides include sucrose, maltose and like disaccharides, mannitol, sorbitol and like sugar alcohols. Examples of amino acids include glycine, alanine and the like.

The buffer may be any of the pharmaceutically acceptable ones but a phosphoric acid buffer is preferable.

The dose of the ameliorant of the invention varies depending on various factors such as the severity of disease, age and body weight of the hepatitis C patient to be treated. The amount of IFN-γ per dose is usually selected from the range of 1000 IU/body to $200 \times 10^6$ IU/body, preferably from the range of $10 \times 10^6$ IU/body to $100 \times 10^6$ IU/body.

It is recommendable that such dose of the ameliorant be continuously administered by incorporation into IFN-α or in combination with the administration of IFN-α for 1 day to 24 weeks, preferably for 2 to 24 weeks.

As described above, the ameliorant of the invention is used by adding and mixing it with IFN-α or used in combination with the administration of IFN-α. The amount of IFN-α used in combination with the ameliorant of the invention is selected from the range of 100 to $1000 \times 10^6$ IU/body per dose, preferably from the range of $1 \times 10^6$ to $1000 \times 10^6$ IU/body per dose. The IFN-α pharmaceutical is preferably administered intramuscularly or subcutaneously in said amount for 1 week to 1 year, preferably for 2 weeks to 6 months.

As regards IFN-γ added to IFN-α or used in combination with IFN-α, the mixing ratio of IFN-γ to IFN-α or the dose of IFN-γ is not limited specifically but may be suitably selected in accordance with the severity of disease of the hepatitis C patient to be treated, etc. For example, in the case of using purified IFN-α and IFN-γ which substantially do not contain any impurities, the mixing ratio or administration ratio of IFN-α to IFN-γ is suitably selected from 1:1 to 100:1, preferably from 1:1 to 10:1 (titer ratio).

The ameliorant of the invention is used in combination with IFN-α or preferably used before the administration of IFN-α, whereby enhancing the hepatitis C therapeutic effects of IFN-α and making the patients continuously HCV-RNA negative. The ameliorant of the invention is especially effective in the treatment of hepatitis C on which a single use of IFN-α produces no effects or does not produce any significant effects, i.e., IFN-α intractable hepatitis C. The ameliorant used in combination with IFN-α can produce therapeutic. effects on the IFN-α intractable hepatitis C. The ameliorant of the invention is useful as an adjuvant for hepatitis C complete recovery in the hepatitis C treatment using IFN-α.

The present invention provides a therapeutic composition for the treatment of hepatitis C comprising IFN-α and IFN-γ as active ingredients.

Like IFN-γ, IFN-α used in the invention may be any of those clinically used and can be of natural type or recombinant type.

The ratio of IFN-α to IFN-γ in the hepatitis C therapeutic composition of the invention may be, for example, in the range of 1:1 to 100:1, preferably the range of 1:1 to 10:1 (titer ratio) in the case of using purified IFN-α and IFN-γ as mentioned above.

The hepatitis C therapeutic composition of the invention essentially comprises IFN-α and IFN-γ and may further contain pharmaceutically acceptable carriers or various kinds of additives as mentioned above in the preparation of the ameliorant in accordance with the pharmaceutical form, as long as they do not counteract the effect of the invention.

It is preferable for the composition to contain the above-mentioned pharmaceutically acceptable carriers or additives such as stabilizers, buffers or the like in addition to IFN-α and IFN-γ.

The hepatitis C therapeutic composition of the invention produces significantly high therapeutic effects on hepatitis C patients, especially IFN-α intractable hepatitis C on which a single use of IFN-α produces no effects or does not produce any significant effects.

As long as the intended effects are produced, there is no specific limitation on the administration timing, administration route and administration form. Any mode mentioned above may be used. The administration form is not limited but injections and drops are preferable and these can be preferably administered intramuscularly or subcutaneously.

The dose of the hepatitis C therapeutic composition of the invention may be such that the amount of IFN-α per dose is within the range of 100 to $1000 \times 10^6$ IU/body, preferably the range of $1 \times 10^6$ to $1000 \times 10^6$ IU/body. It is desirable the amount of IFN-γ per dose be within the range of 1000 to $200 \times 10^6$ IU/body, preferably the range of $10 \times 10^6$ to $100 \times 10^6$ I U/body. Preferably, the hepatitis C therapeutic composition is continuously administered for 1 day to 24 weeks, more preferably for 2 to 24 weeks.

The composition of the invention may be used in combination with the administration of a pharmaceutical comprising IFN-α as an active ingredient. That is, while the IFN-α pharmaceutical is continuously administered for 1 week to 1 year, preferably for 2 weeks to 6 months, the hepatitis C therapeutic composition of the invention can be intermittently administered.

The present invention further provides an effective therapeutic method for the treatment of hepatitis C.

As mentioned above, the therapeutic method of the invention may be a method comprising administering a hepatitis C therapeutic composition comprising effective amounts of IFN-α and IFN-γ to a patient, a method comprising separately administering effective amounts of IFN-α and IFN-γ to a patient at the same time, or a method comprising administering an effective amount of IFN-α after administering an effective amount of IFN-γ. Preferable is the method comprising administering IFN-α after the administration of IFN-γ.

The doses and administration ratio of IFN-α to IFN-γ may be the same as mentioned above. Stated more specifically, the dose of IFN-γ is not limited but may be selected from the range of 1000 IU to $200 \times 10^6$ IU/body, preferably the range of $10 \times 10^6$ to $100 \times 10^6$ IU/body. IFN-γ is continuously administered every day or every two or three days for 1 day to 24 weeks, preferably for 2 to 24 weeks. Subsequently, IFN-α is administered. The dose of IFN-α may be selected within the range of 100 to $1000 \times 10^6$ IU/body, preferably the range of $10 \times 10^6$ to $1000 \times 10^6$ IU/body. IFN-α is preferably administered in an amount of 1 to 100 titers, more preferably 1 to 10 titers, per titer of IFN-γ (dose) previously administered. The administration period of IFN-α is not limited specifically but is usually 1 week to 1 year, preferably 2 weeks to 6 months. During the period, IFN-α is preferably administered continuously every day or every two or three days.

Administration of IFN-α and IFN-γ according to the above method can enhance hepatitis C therapeutic effect (action of making the patient HCV-RNA negative).

The above method can bring about significantly high therapeutic effects on hepatitis C on which a single use of IFN-α produces no effects or does not produce any significant effects, i.e., IFN-α intractable hepatitis C. Therefore, the therapeutic method of the invention is especially useful for the treatment of IFN-α intractable hepatitis C patients.

The present invention further provides a pharmaceutical kit useful in the above hepatitis C therapeutic method, particularly the method in accordance with the administration schedule comprising administering IFN-α after administration of IFN-γ. More specifically the present invention provides a kit for the treatment of hepatitis C, separately containing at least an IFN-α pharmaceutical and an IFN-γ pharmaceutical. The IFN-α pharmaceutical or the IFN-γ pharmaceutical essentially comprises IFN-α or IFN-γ as an active ingredient and may further contain pharmaceutically acceptable carriers or additives. Examples thereof include pharmaceuticals mentioned above.

The proportion of IFN-α or IFN-γ in the pharmaceutical and the administration ratio of IFN-α pharmaceutical to IFN-γ pharmaceutical may be the same as mentioned above.

BEST MODE FOR CARRYING OUT THE INVENTION

The present invention is described below with reference to Examples. The invention is in no way limited by the examples.

Example 1

IFN-α intractable chronic hepatitis C patients, i.e., IFN-α-ineffective patients with HCV genotype 1b and a large amount of virus who had failed to respond to the first administration of IFN-α were used as subjects. IFN-γ ($1 \times 10^6$ IU/body per dose) was administered to each patient (intramuscular injection) every day for 2 weeks, followed by the administration of IFN-α ($5 \times 10^6$ IU/body per dose) every day for 2 weeks, and further IFN-α was intermittently administered three times weekly for 22 weeks (this group is thereinafter referred to as "IFN-γ combined use treatment group").

As a control treatment group, hepatitis C patients satisfying the similar condition received intramascular injections of only IFN-α ($5 \times 10^6$ IU/body per dose) according to the same schedule. This group is referred to as "IFN-α re-administration treatment group". The results of this group were compared with the cases of the present invention.

The results show that HCV-RNA negative rate achieved after two weeks of IFN-α administration was 12.5% in the control "IFN-α re-administration treatment group", whereas it was 36.4% in the "IFN-γ combined use treatment group" of the present invention and the remarkable efficacy (HCV-RNA continuous negative rate) was 25.0%. "HCV-RNA continuous negative" means that the patient was HCV-RNA negative 6 months after the completion of administration. If the patient is HCV-RNA negative 6 months after the administration, the negative state will continue thereafter and hepatitis C is considered to cure completely.

|  | HCV-RNA negative rate after 2 weeks of administration | Remarkable efficacy HCV-RNA continuous negative rate |
|---|---|---|
| Present invention treatment group | 36.4% (8/22) | 25.0% (1/4) |
| IFN-α re-administration treatment | 12.5% (1/8) | |

As is clear from the above results, the administration of IFN-γ prior to the IFN-α administration triplicated the HCV-RNA negative rate, as compared to the single use of IFN-α. Moreover, HCV-RNA continuous negative rate, which was conventionally reported to be extremely low, remarkably increased to 25%.

When IFN-α and IFN-γ were separately administered to IFN-α intractable chronic hepatitis C patients at the same time in place of using the above method of administering IFN-γ prior to the IFN-α administration, the HCV-RNA negative rate significantly increased.

By contrast, when IFN-α was administered for 24 weeks and thereafter IFN-γ was administered for 2 weeks (14 cases) in place of the above method, HCV-RNA continuous negative rate was 0% (0/14).

Example 2

It has been reported that when wild type strains having no mutation in the NS5A region (non-structural region) of the gene sequence are dominant in HCV of genotype 1b, therapeutic effects of IFN-α are extremely low, whereas IFN-α produces therapeutic effects when mutant strains (mutant type) having mutation are dominant.

This time, IFN-α ($5 \times 10^6$ IU) was re-administered every day for 2 weeks to 8 chronic hepatitis C patients with wild-type strain-dominant HCV of genotype 1b, who had failed to respond to the IFN-α administration. No decrease of virus was observed. Further, when IFN-γ was administered every day for 2 weeks, there were cases in which the dominant strain changed from the wild type to the mutant. In such cases, when IFN-α ($5 \times 10^6$ IU) was intermittently administered for 22 weeks, the patients became HCV-negative.

What is claimed is:

1. A therapeutic method for the treatment of hepatitis C, which comprises administering therapeutically effective amounts of interferon-α and interferon-γ to a subject at the same time or administering a therapeutically effective amount of interferon-γ before the administration of a therapeutically effective amount of interferon-α.

2. A therapeutic method for the treatment of hepatitis C, which comprises administering a therapeutically effective amount of interferon-γ to a subject before the administration of a therapeutically effective amount of interferon-α.

3. The therapeutic method for the treatment of hepatitis C according to claim 2, which comprises continuously administering interferon-γ for 2 to 24 weeks and then continuously administering interferon-α for 2 to 24 weeks.

4. The therapeutic method of claim 1 or 2 wherein the hepatitis C is chronic hepatitis C intractable with interferon-α.

5. The therapeutic method of claim 1 or 2, wherein said interferon-α and interferon-γ are administered by a route selected from the group consisting of oral, parenteral, local, general, intramuscular, subcutaneous, and intravenous.

6. The therapeutic method of claim 5, wherein said route is selected from the group consisting of intramuscular and subcutaneous.

7. The therapeutic method of claim 1 or 2, wherein said interferon-γ is administered in an amount of 1000 IU/body per dose to $200 \times 10^6$ IU/body per dose.

8. The therapeutic method of claim 1 or 2, wherein said interferon-γ is administered for one day to 24 weeks.

9. The therapeutic method of claim 1 or 2, wherein said interferon-a is administered in an amount of 100 IU/body per dose to $1000 \times 10^6$ IU/body per dose.

10. The therapeutic method of claim 9, wherein said interferon-α is administered in an amount of $1\times10^6$ IU/body per dose to $1000\times10^6$ IU/body per dose.

11. The therapeutic method of claim 1 or 2, wherein said interferon-α is administered for one week to one year.

12. The therapeutic method of claim 11, wherein said interferon-α is administered for two weeks to six months.

13. The therapeutic method of claim 1, wherein said interferon-α and said interferon-γ are administered to said subject at the same time and the ratio of interferon-a to interferon-γ is 1:1 to 100:1.

* * * * *